United States Patent
Quinn (10) Patent No.: US 6,517,529 B1
(45) Date of Patent: Feb. 11, 2003

(54) HEMODIALYSIS CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 154 days.

(21) Appl. No.: 09/651,763

(22) Filed: Aug. 30, 2000

Related U.S. Application Data (63) Continuation-in-part of application No. 09/448,130, filed on Nov. 24, 1999, now abandoned.

(51) Int. Cl.[7] ............................................. A61M 25/01
(52) U.S. Cl. ..................... 604/528; 604/6.16; 604/541
(58) Field of Search ............................... 604/541, 264, 604/266, 270, 523, 528, 4.01–6.05, 6.16

(56) References Cited

U.S. PATENT DOCUMENTS

| | | |
|---|---|---|
| 1,879,249 A | 9/1932 | Honsaker |
| 2,116,083 A | 5/1938 | Rusch |
| 3,384,089 A | 5/1968 | Shriner |
| 3,589,368 A | 6/1971 | Jackson et al. |
| 4,037,599 A | 7/1977 | Raulerson |
| 4,134,402 A | 1/1979 | Mahurkar |
| 4,270,542 A | 6/1981 | Plumley |
| 4,311,140 A | 1/1982 | Bridgman |
| 4,368,737 A | 1/1983 | Ash |
| 4,381,011 A | 4/1983 | Somers, III |
| 4,445,897 A | 5/1984 | Ekbladh et al. |
| 4,498,902 A | 2/1985 | Ash et al. |
| 4,529,399 A | 7/1985 | Groshong et al. |
| 4,549,879 A | 10/1985 | Groshong et al. |
| 4,559,039 A | 12/1985 | Ash et al. |
| 4,568,329 A | 2/1986 | Mahurkar |
| 4,583,968 A | 4/1986 | Mahurkar |
| 4,623,327 A | 11/1986 | Mahurkar |
| 4,639,252 A | 1/1987 | Kelly et al. |
| 4,671,796 A | 6/1987 | Groshong et al. |
| 4,692,141 A | 9/1987 | Mahurkar |
| 4,692,153 A | 9/1987 | Berlin et al. |
| 4,701,166 A | 10/1987 | Groshong et al. |
| 4,770,652 A | 9/1988 | Mahurkar |
| 4,772,266 A | 9/1988 | Groshong |
| 4,781,678 A | 11/1988 | de Couët et al. |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 5,053,004 A | 10/1991 | Markel et al. |
| 5,197,951 A | 3/1993 | Mahurkar |
| 5,221,255 A | 6/1993 | Mahurkar et al. |
| 5,221,256 A | 6/1993 | Mahurkar |
| 5,322,519 A | 6/1994 | Ash |
| 5,336,177 A | 8/1994 | Marcus |
| 5,374,245 A | 12/1994 | Mahurkar |
| 5,378,230 A | 1/1995 | Mahurkar |
| 5,451,216 A | 9/1995 | Quinn |
| 5,486,159 A | 1/1996 | Mahurkar |
| 5,571,093 A | 11/1996 | Cruz et al. |
| 5,599,322 A | 2/1997 | Quinn |
| 5,607,405 A | 3/1997 | Decker et al. |
| 5,624,413 A | 4/1997 | Markel et al. |
| 5,685,836 A | 11/1997 | DiPerna et al. |
| 5,776,111 A | 7/1998 | Tesio |
| 5,947,953 A | 9/1999 | Ash et al. |
| 5,984,913 A | 11/1999 | Kritzinger et al. |

FOREIGN PATENT DOCUMENTS

GB 745379 2/1956

*Primary Examiner*—Brian L. Casler
*Assistant Examiner*—Jeremy Thissell
(74) *Attorney, Agent, or Firm*—Brinks Hofer Gilson & Lione

(57) ABSTRACT

A hemodialysis catheter comprising a lumen tube with a bolus at its distal end. A main venous port is formed in one side of the bolus adjacent the bullet nose of the bolus. Second and third venous ports are formed in either the bolus or the tube. The second port is circumferentially displaced 180° around the catheter from the main venous port. An arterial port is formed in either the bolus or the tube, in axial alignment with the main venous port and circumferentially displaced 180° around the catheter from the second venous port.

16 Claims, 4 Drawing Sheets

HEMODIALYSIS CATHETER

RELATED APPLICATION

This is a continuation-in-part of application Ser. No. 09/448,130, filed Nov. 24, 1999, now abandoned, and entitled HEMODIALYSIS CATHETER.

FIELD OF THE INVENTION

This invention relates in general to hemodialysis. It relates, more particularly, to hemodialysis catheters.

BACKGROUND OF THE INVENTION

Hemodialysis, as practiced today, normally employs one of two types of hemodialysis catheter to remove blood from the patient for processing and return processed blood to the patient. Most commonly, a tube containing two lumens is used, each lumen having a generally semi-cylindrical or D-shape configuration. This type of catheter is frequently referred to as a dual lumen catheter. Alternatively, two separate tubes, each with a full cylindrical configuration, are used to remove blood for dialysis and return the processed blood.

Flow rates possible with conventional dual lumen catheters are usually lower than those achievable where separate tubular lumens are used to remove blood from a vein for dialysis and then return processed blood back to the vein. Thus, two tube lumens have become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein (the venous line) and the line removing blood for purification (the arterial or intake line) at flow rates above 300 ml per minute. A high flow rate from the venous line can cause whipping or "firehosing" of the tip in the vein with consequent damage to the vein lining. A corresponding high flow rate into the arterial line causes the port to be sucked into the vein wall, resulting in occlusion. It should be understood, of course, that both lines normally access the superior vena cava and the designations are used for differentiation purposes.

Speed of flow through a catheter lumen, whether it be in a single lumen or a dual lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force, of course. This is a positive pressure pushing processed blood through the venous lumen and a negative (suction) pressure pulling unprocessed blood through the arterial lumen.

Problems encountered in providing for a high flow rate through a catheter are magnified in a dual lumen catheter construction. Because each of the lumens in a dual lumen catheter has a D-shape, it has been assumed that flow rates are limited. Furthermore, such dual lumen catheters are, to a great extent, catheters with a main port, which opens at the end of a lumen substantially on the axis of the lumen. Thus, firehosing frequently results. There are dual lumen catheters which utilize side ports for both outflow and inflow. An example is the catheter disclosed in the Cruz et al. U.S. Pat. No. 5,571,093. However, such catheters have not been successful in solving numerous problems related to hemodialysis with dual lumen catheters, e.g., high incidences of catheter port occlusion as well as some degree of fire-hosing still occurs.

SUMMARY OF THE INVENTION

An object of the present invention is to provide an improved hemodialysis catheter.

Another object is to provide an improved dual lumen hemodialysis catheter.

Another object is to provide a dual lumen hemodialysis catheter which accommodates flow rates substantially as high as the latest separate lumen catheters.

Still another object is to provide a dual lumen hemodialysis catheter which is capable of returning processed blood to the patient at high flow rates without harmful firehosing of the catheter tip.

Yet another object is to provide a dual lumen hemodialysis catheter which permits high flow rates while minimizing trauma and potential red cell damage so as to substantially avoid clotting.

A further object is to provide a dual lumen hemodialysis catheter which substantially reduces the incidence of port occlusion.

Still a further object is to provide a dual lumen hemodialysis catheter in which occlusion of the return line port is substantially avoided regardless of the flow rate.

Yet a further object is to provide a new and improved bolus design and construction in a dual lumen hemodialysis catheter.

The foregoing and other objects are realized in accord with the present invention by providing a hemodialysis catheter including a dual lumen catheter tube, a bullet-nose bolus having a radially extending main outflow or venous port, at least one additional outflow or venous port radially extending through either the bolus or the tube and at least one intake or arterial port radially extending through the bolus or the tube. An additional outflow port is circumferentially displaced 180° around the tube from the main outflow port, and axially displaced from the main outflow port. A main intake port is circumferentially displaced 180° around the tube from the additional outflow port. The use of such bolus, port and dual lumen tube combinations produces high flow rates, maximum diffusion, minimum occlusion and minimum vein wall damage in a dual lumen hemodialysis catheter.

In a first embodiment of the invention, the arterial and the venous lumens open through a radially extending main venous port and an intake or arterial port which are immediately adjacent each other on one side of the bolus next to the bullet nose in the bolus. The venous lumen also opens through a second outflow port formed in the tube adjacent the bolus and circumferentially displaced 180° around the axis of the catheter tube from the main venous port. Directly opposite this second venous port, the tube body wall is thickened in an oval pattern to form a longitudinally elongated bulge. The bulge forms a stiffening arch in the tube wall and prevents buckling of the tube at the second venous or outflow port.

In a second embodiment of the invention, the venous and arterial lumens open through radially extending, axially displaced main outflow and intake ports on the same side of the catheter bolus. A main outflow port for the venous lumen port is formed radially in the bolus adjacent its bullet nose.

A second outflow port for the venous lumen is formed radially in the bolus, circumferentially removed 180° from the main port, and displaced axially from the main port. A third outflow port is formed radially in the bolus, axially aligned with the main outflow port and axially displaced from both the main and second outflow ports. A main inflow or arterial port is formed radially in the bolus at a point axially displaced in the bolus from the outflow ports.

In the second embodiment, directly opposite each of the second and third outflow ports and the main intake port, the tube body wall is thickened in an oval pattern to form a longitudinally elongated bulge. Each bulge forms a stiffening arch in the bolus and prevents buckling of the bolus at the corresponding ports.

In this embodiment, the dual lumen tube is a 13.5 French tube, giving it a nominal O.D. of 0.180 inches. The bolus, on the other hand, is 10 French size, i.e., it has a nominal O.D. of 0.136 inches. The catheter tip tapers from the 13.5 French size to the 10 French size between the second and third ports. As such, the inflow lumen has a D-shape until it reaches a tapered middle of the bolus, whereupon it transitions to a circular cross-section. At the same time the cross-sectional area of the lumen increases from 0.005 $in^2$ to 0.006 $in^2$.

In a conventional dual lumen catheter, substantially the entire volume and pumping force of returning processed blood is directed primarily out of the end of the outflow lumen because of the orientation of the end port and the size and shape of any conventional side ports employed. Little processed blood actually flows out through side ports. The present invention allows higher outflow and inflow rates. The redirection of a portion of the outflow through side ports separated from the main port reduces the speed and force of the outflow from the main port. Fluid pressure is reduced before the outflow reaches the main port. This reduction in force results in better diffusion and protects against whipping and cell destruction. The intake port is positioned and configured to prevent clogging and occlusion due to "vein wall sucking." In addition, both port configurations are smooth and without sharp edges whereby damage to blood cells is greatly reduced.

BRIEF DESCRIPTION OF THE DRAWINGS

The invention, including its construction and method of operation, is illustrated more or less diagrammatically in the drawings in which.

DESCRIPTION OF THE PREFERRED EMBODIMENTS

Figure 1:
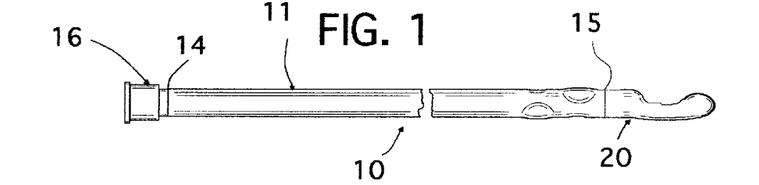
FIG. 1 is a side elevational view of a first embodiment of the hemodialysis catheter comprising features of the present invention.

Referring now to the drawings, and particularly to FIG. 1, a dual lumen hemodialysis catheter comprising a first embodiment of the invention is illustrated generally at 10. The catheter 10 comprises a cylindrical tube 11 having a proximal end 14 and a distal end 15. A bolus 20 is attached to the distal end 15.

Referring also to FIGS. 3–9, the tube 11 is a 13.5 French tube formed of silicone. The tube 11 comprises a tubular body 24 with a generally cylindrical wall 25 having a thickness of 0.040 inches. The body 24 is divided by a septum 26 which defines two identical, D-shape lumens 27A and 27B extending through the body along its length. Arterial lumen 27A and venous lumen 27B each have a D-shape cross-sectional area of 0.005 inches.

The distal end 15 of the tube 11 joins the bolus 20 at the line 31. Forward of the line 31, the tube body 24 has a necked down end 33 which is seated in a suitably formed socket 34 in the bolus 20 and glued or welded to the bolus.

The tube body 24 has a venous port 35 and an arterial port 37 formed radially through it adjacent the distal end 15 of the tube 11, and longitudinally spaced from each other. The ports 35 and 37 are, in addition to being longitudinally spaced, also displaced 180° from each other circumferentially around the axis of the tube body 124. On compass point terms, the port 35 is at 180° and the port 37 is at 0°/360°. The port 35 communicates with the venous lumen 27B and the port 37 with the arterial lumen 27A.

The ports 35 and 37 are identical to each other. Accordingly, only the port 37 will be described. The port 37 is formed through the tube body wall 25 during molding so as to have a racetrack shape longitudinally of the tube 11. The port 37 is 0.040 inches long and 0.020 inches wide.

The edge 39 of the racetrack shaped port 37 is semi-circular in cross-section, i.e., rounded along its entire length. The wall 25 is 0.040 inches thick where the port 37 is formed. Thus, the radius of the semi-circular edge 39 is 0.020 inches.

Figure 2:
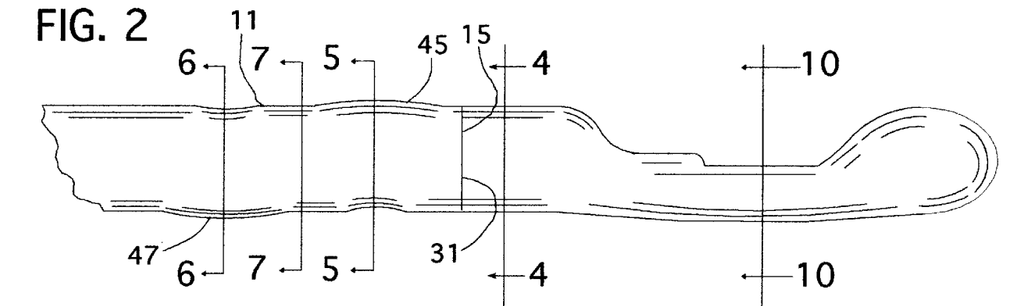
FIG. 2 is an enlarged side elevational view of the tip end of the catheter in FIG. 1.

The second and third ports 35 and 37 are spaced longitudinally so that their centerlines, seen at the section lines 5—5 and 6—6 in FIG. 2, are 0.175 inches apart. The centerline of the arterial port 35 is, in turn, spaced 0.175 inches from the centerline of the bolus 20 ports, hereinafter described.

Immediately opposite each of the ports 35 and 37 in the tube wall 25, the wall is thickened in an oval pattern to form an elongated bulge. At its thickest, each bulge 45 and 47 is about 40% thicker than the rest of the tube wall 25. The bulge is centered on the corresponding port opposite it Thus, a stiffening arch is formed In the tube wall 25 opposite each port.

The bolus 20 has a body 51 also formed of silicone. The dimensions of the body 51 will vary with the size of the catheter tube 11 in use, but in the present illustration they are those of the 13.5 French tube.

Figure 3:
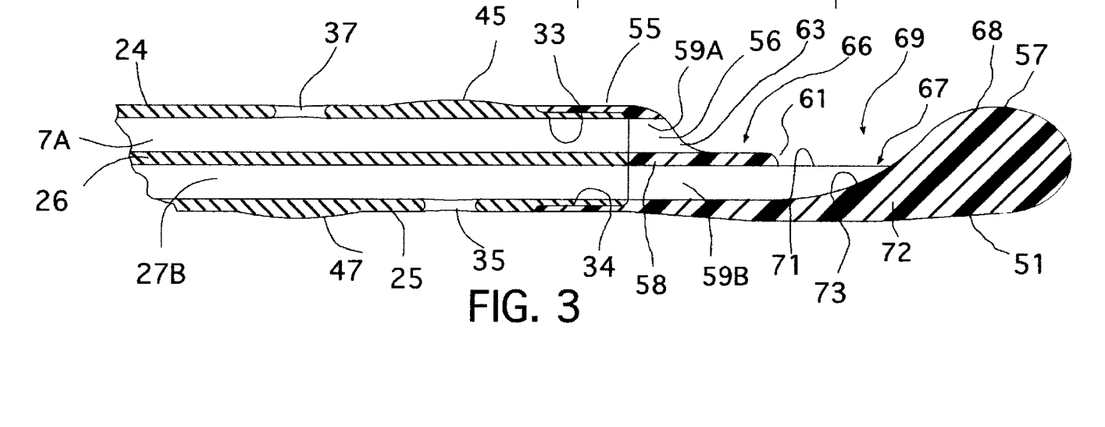
FIG. 3 is a longitudinal sectional view taken through the catheter seen in FIG. 2.
Figures 4, 5, 6, 7, 8:
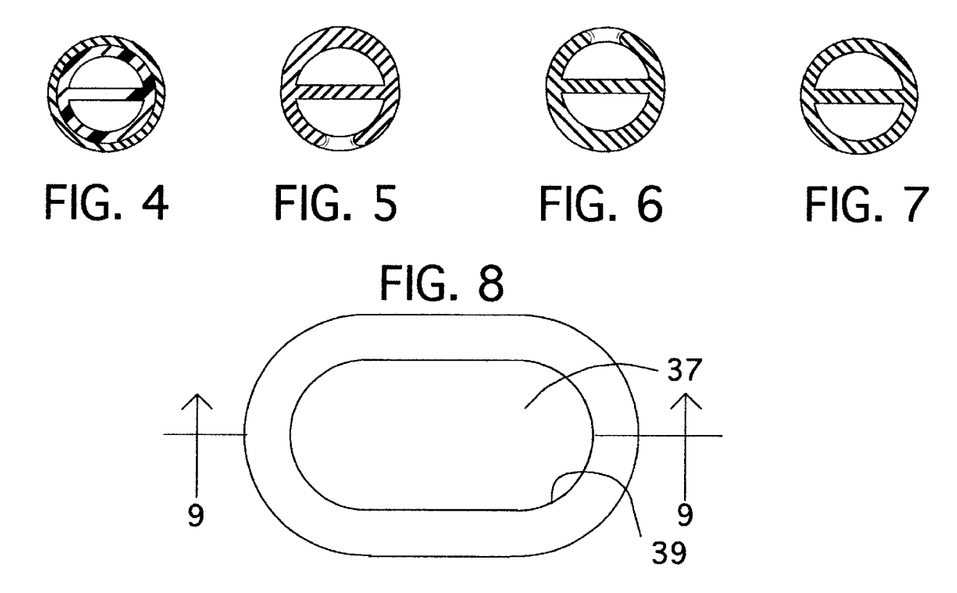
FIG. 4 is a sectional view taken along line 4—4 of FIG. 2.
FIG. 5 is a sectional view taken along line 5—5 of FIG. 2.
FIG. 6 is a sectional view taken along line 6—6 of FIG. 2.
FIG. 7 is a sectional view taken along line 7—7 of FIG. 2.
FIG. 8 is an enlarged plan view of one of the catheter tube ports in the catheter of FIGS. 1 and 2.
Figure 9:
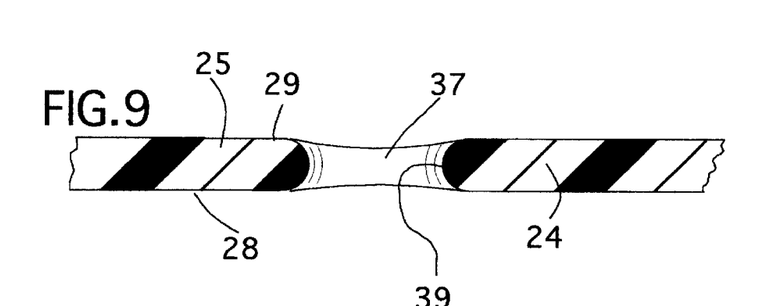
FIG. 9 is a sectional view taken along line 9—9 of FIG. 8.
Figure 10:
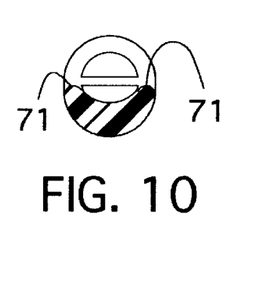
FIG. 10 is a sectional view taken along line 10—10 of FIG. 2.
Figure 11:
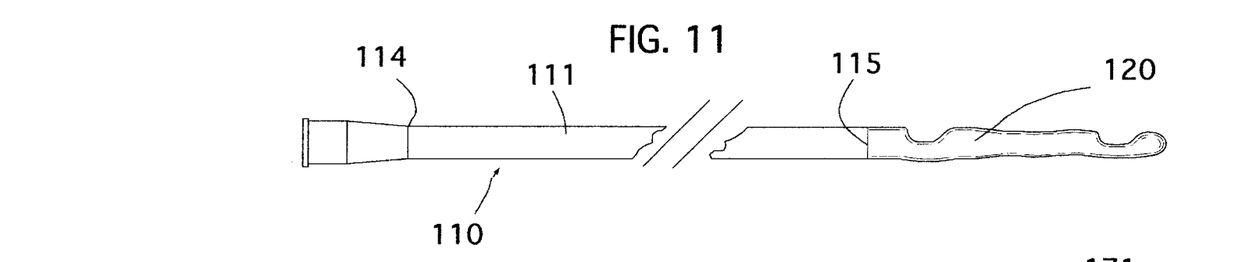
FIG. 11 is a side elevational view of a second embodiment of the hemodialysis catheter comprising features of the invention, with parts removed.
Figure 12:
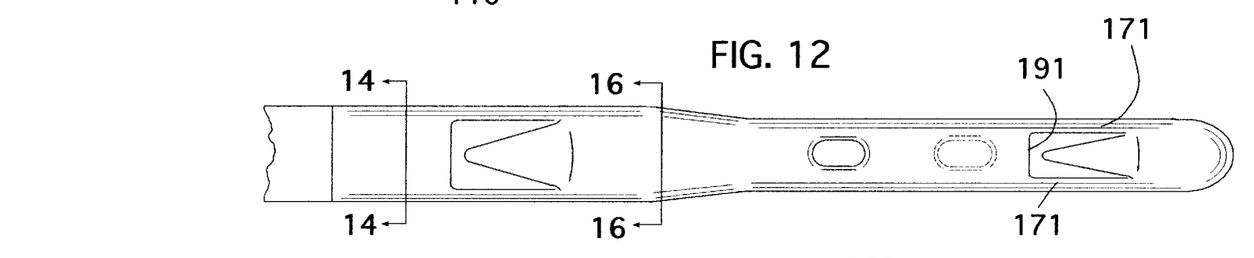
FIG. 12 is a top plan view of the bolus end of the catheter of FIG. 11.

The bolus body 51 has a tube connector section 55, a flow passage section 56 and a bullet nose section 57. The tube connector section 55 has a septum 58 formed in it. The septum 58 mates, end-to-end, with the septum 26 in the tube body 24, as best seen in FIG. 3. The septum 26 then extends into the flow passage section 56. The septum 58 divides the flow passage section 56 into an upper arterial passage 59A and a lower venous passage 59B.

The lumens 27A and 27B in the tube body 24 communicate with the passages 59A and 59B in the bolus body 51 through the connector section 55, above and below the septum 58. The passage 59B extends to the end 61 of the septum 58 where it enters a radial passage 67 having a base 68 which curves across the axis of the body 51 to form one end of a main outflow or venous port 69 in the body. The outflow port 69 is enlarged circumferentially by forming low sides 71 for the radial passage 67 so that the port 69 extends circumferentially around about 190° of the axis of the body 51.

The passage 59A opens at 63, above the septum 58, short of the end 61 of the septum. There, a radial intake or arterial port 66 is formed in the bolus above the level of the septum 58 and extending circumferentially around about 175° of the axis of the body 61. The arterial port 66 and the venous port 69 together form one continuous opening on the side of the bolus body 51 between the connector section 55 and the bullet nose section 57.

Directly opposite the center of the combined ports 66 and 69, the floor 72 of the radial passage 67 is thickened, as at 73, to form a stiffening arch in the bolus 20. The arch 73 begins at about the end of the tube body 24, increases in thickness until it is directly under the ports 66 and 69, and then decreases in thickness to the bullet nose section 57.

The port 69 is a venous or outflow port for the venous lumen 27B, as has been pointed out. Outflow is around the end of the septum 58 and forwardly over the bullet nose section 57 of the bolus body 51.

The port 35 is also a venous or outflow port, as has been pointed out. Outflow through the port 35 is directed opposite the catheter axis from that of the port 69, because the port 35 is 180° displaced from the port 69.

The port 66 is an arterial or intake port for the arterial lumen 27A, as has also been pointed out. Intake is above the lumen 58, axially displaced from the outflow of the port 69.

The port 37 is also an arterial or intake port, as previously pointed out. It communicates with the upper or arterial lumen 27A in the tube 11.

Referring now to FIGS. 11–19, a second embodiment of dual lumen catheter comprising features of the invention is illustrated generally at 110. The catheter 110 comprises a cylindrical tube 111 having a proximal end 114 and a distal end 115. A bolus 120 is attached to the distal end 115.

The tube 111 is a 13.5 French tube formed of silicone. The tube 111 comprises a tubular body 124 with a generally cylindrical wall 125 having a thickness of 0.040 inches. The body 124 is divided by a septum 126 which defines two identical D-shape lumens 127A and 27B extending through the body along its length. The lumen 127A is an arterial lumen and the lumen 127B is a venous lumen. Each lumen 127A and 127B has a cross-sectional area of 0.005 inches.

The distal end 115 of the dual lumen tube 111 joins the bolus 120 at 131. Here, the tube body 124 has a necked down end 133 which is seated in a suitably formed socket 134 in the bolus 120. The bolus 120 has a body 151 also formed of silicone. The tube 111 and bolus 120 are mated in this fashion after each is formed of raw silicone. The silicone is then cured. When cured, mated portions of the tube 111 and the bolus 120 are effectively welded together.

The bolus body 151 is 1.46 inches long. The body 151 includes a tube connector section 155, a flow passage section 156 and a bullet nose section 157.

Figure 13:
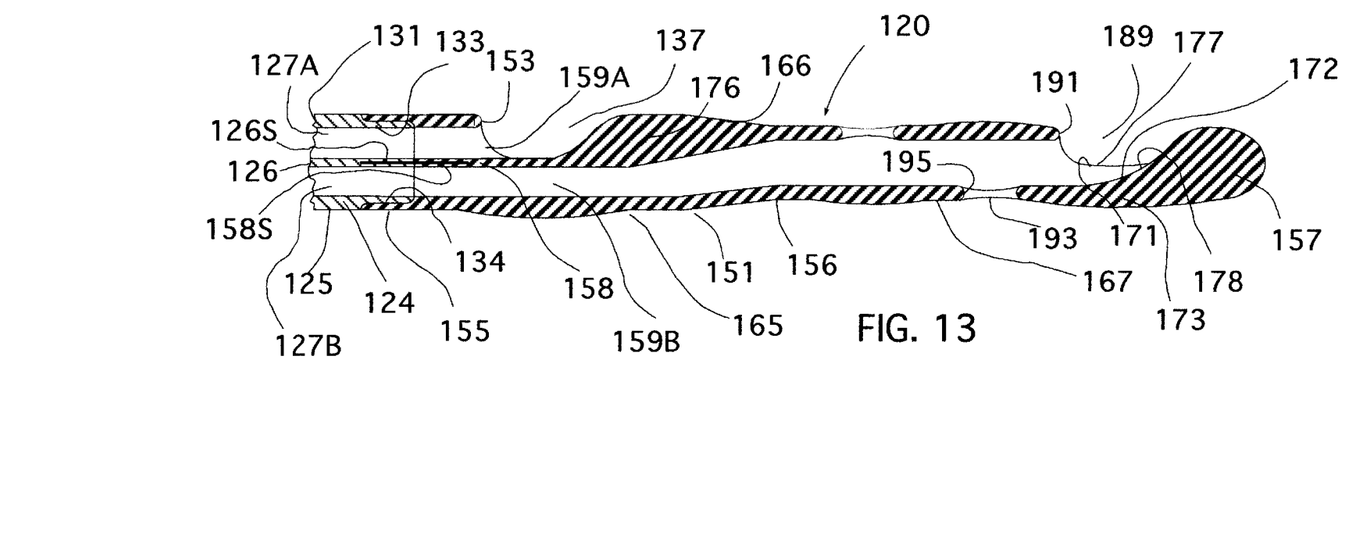
FIG. 13 is a longitudinal sectional view through the bolus end of the catheter seen in FIG. 12.
Figure 14:
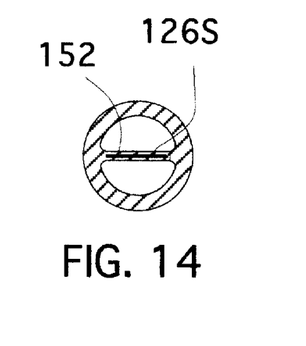
FIG. 14 is a sectional view taken along line 14—14 of FIG. 12.

The tube connector section 155 is a 13.5 French diameter section which is 2.00 inches long and has a septum 158 formed in it. The septum 158 mates, end-to-end with the septum 126 in the tube body 126. As best seen in FIGS. 13 and 14, a slit 126S is formed into the end of the septum 126, halfway between its upper and lower surfaces. A corresponding slit 158S is formed into the end of the septum 158. These slits receive a 0.005 inch thick nylon card 152 which aligns the opposed ends of the lumens 126 and 158 so that they will bond together.

The septum 158 forms D-shape upper and lower passages 159A and 159B in the tube connector section 155. Each has a cross-sectional area of 0.005 inches. The upper passage 159A is an arterial passage. The lower passage 159B is a venous passage.

Extending forwardly from the tube connector section 155 is the flow passage section 156 of the bolus body 151. The flow passage section 156 is 1.062 inches long and comprises three axially aligned sub-sections, a 13.5 French sub-section 165, a transition sub-section 166 and a 10 French sub-section 167.

The 13.5 French sub-section 165 is 0.400 inches long. The transition sub-section 166 is 0.175 inches long and the 10 French sub-section 167 is 0.497 inches long. The nominal O.D. of the 13.5 French sub-section 165 is 0.180 inches while the nominal O.D. of the 10 French sub-section 167 is 0.136 inches.

The 13.5 French sub-section 165 contains continuations of upper arterial passage 159A and lower venous passage 159B. The lower venous passage 159B has a uniformly dimensional D-shape, as seen in FIG. 14, for 0.300 inches of its length. The cross-sectional area is 0.005 in$^2$. Then the passage 159B begins to change in shape and increase in cross-sectional area in a manner which will subsequently be discussed.

Figure 15:
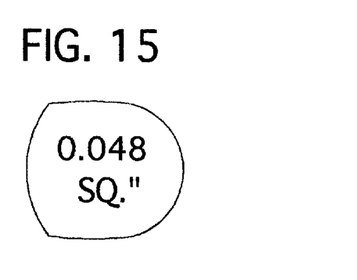
FIG. 15 is an expanded top plan view of the outflow or venous port in the bolus end of the catheter of FIG. 11.
Figure 16:
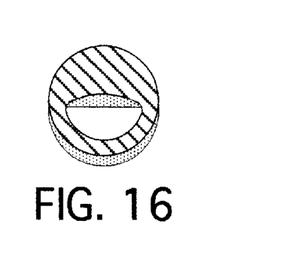
FIG. 16 is a sectional view taken along line 16—16 of FIG. 12.
Figure 17:
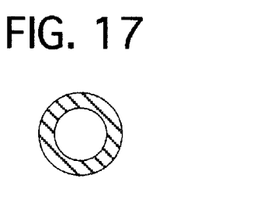
FIG. 17 is a sectional view taken along line 17—17 of FIG. 12.

The upper arterial passage 159A in the 13.5 French sub-section 165 extends forwardly above the septum 158 to the radial main arterial port 137. The radial arterial port 137 is 0.265 inches long at the outer surface of the bolus body 151 and extends circumferentially around the body's axis from the upper surface of the septum 158 on one side of the tube to the upper surface of the septum in its other side. As such, the port 137 has a plan cross-sectional area for venous flow of 0.070 inches, as seen in FIG. 15.

The leading edge 153 of the bolus body 151 above the passage 159A (which forms the trailing edge of the port 137) is rounded along its entire length down to the septum, as seen in FIG. 13. The thickness of the 13.5 French body 151 at this edge 173 is 0.026 inches, so the radius of the rounded edges is 0.013 inches.

Forward of the arterial port 137 in the 13.5 French sub-section 165 of the bolus body 151 this sub-section becomes solid, as at 176. In effect, the septum 158 melds into this solid portion 176 of the bolus body 151.

The transition sub-section 166 of the bolus body 151 is externally frusto-conical whereby the bolus body is reduced in size from 13.5 French to 10 French. The aforedescribed solid portion 176 of the 13.5 French sub-section 165 melds into the frusto-conical transition sub-section 166.

Meanwhile, inside the transition sub-section 166, the venous passage 159B changes from a distorted D-shape, where the transition sub-section 166 begins, to a round or cylindrical shape where it ends. The bolus body 151 at this point has the cross-sectional shape and size seen in FIG. 17. It has an internal cross-sectional area of 0.006 in$^2$, the size of a 10 French tube.

The 10 French sub-section 167 of the flow passage section 156 in the bolus body 151 then continues forwardly to the bullet nose section 157 of the bolus body 151. The passage 159B enters a radial passage 177 having a base 178 which curves across the body 151 to form the front end of a main outflow or venous port 189 in the body. The port 189 extends circumferentially around 190° of the body 151 to its side edges 171.

Figure 18:
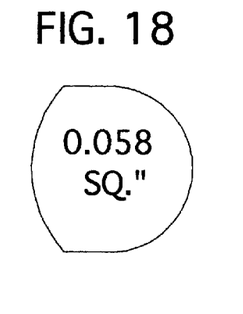
FIG. 18 is an expanded top plan view of the main intake or arterial port in the bolus end of the catheter of FIG. 12.

The port 189 is 0.240 inches long from its trailing edge 191 to the nose section 157 of the bolus body 151. The edge 191 rounded along its entire length, as are the side edges 171, which are continuations of the edge 191. As seen in FIG. 18, the port 189 has an expanded plan area of 0.060 in$^2$.

Directly opposite the center of the port 189, the floor 172 of the radial passage 167 is thickened to form a stiffening arch 173 in the bolus. The arch 173 begins at a second venous port 193 in the bolus body 151, increases in thickness until it is directly under the port 189, and then decreases in thickness to where the passage section 156 joins the bullet nose section 157.

Figure 19:
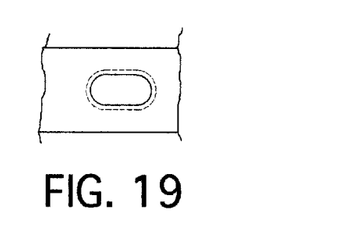
FIG. 19 is a bottom plan view of the second outflow or venous port in the bolus end of the catheter of FIG. 12.

The second venous port 193 has a racetrack shape, as seen in FIG. 19. It is 0.100 inches long and 0.050 inches wide, with a plan cross sectional area of 0.004 in$^2$. The edge 145 of the port 193 is curved along its entire length. The radius of the curve is 0.0125 inches.

The centerline of the second venous port 193 is axially displaced 0.175 inches from the centerline of the main venous port 189. The second port 193 is circumferentially displaced 180° around the bolus body 151 from the main venous port 189.

A third venous port 201 is formed in the passage sub-section 166 displaced axially 0.175 inches from the second port 193. The port 201 is identical in configuration and size to the port 193. It is circumferentially displaced 180° from the port 193 and, as such, is axially aligned with the main venous port 189.

Figure 20:
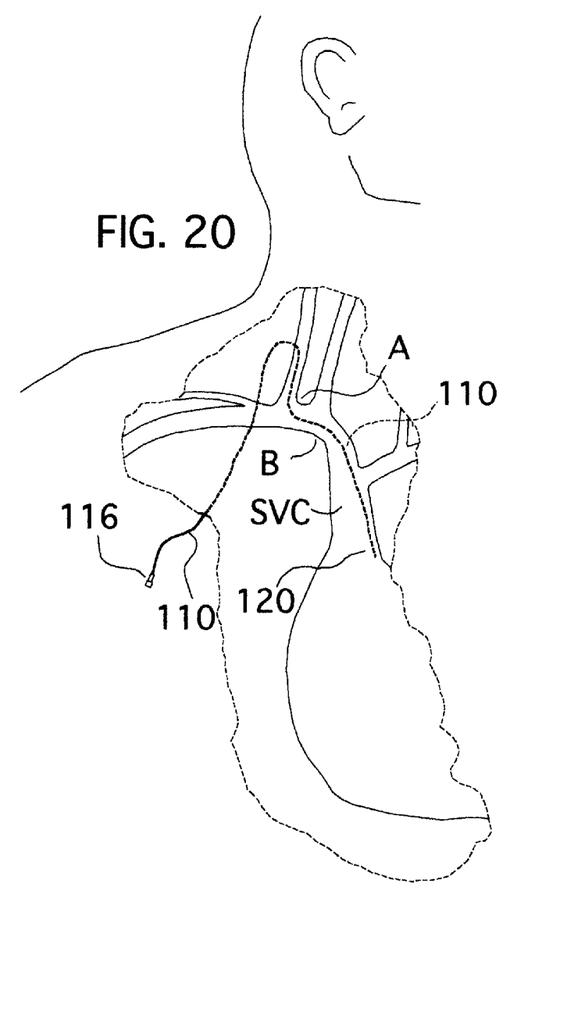
FIG. 20 is a schematic illustration of a catheter installation in a patient.

Referring now to FIG. 20, a catheter 110 is shown there in place in the superior vena cava (SVC) of a patient. The catheter 110 has been introduced through the external jugular vein in the patient's neck and fed through that vein into the SVC.

As will be seen, in following this course the catheter bolus 120 has to lead the catheter 110 around what amounts to two 90° bends in the jugular vein and the SVC. The bends are indicated at A and B. In navigating the bends, the bullet-nosed body 151 of the bolus 120 tends to slide along the surface of the vein wall, without abrading the wall as it passes. As a result, vein wall damage is avoided during insertion; such damage being a common occurrence with conventional catheters.

Although FIG. 20 illustrates insertion of a catheter 110, it should be understood that this second embodiment catheter is used here merely as an example. FIG. 20 could as readily have illustrated placement of a catheter 10 comprising features of the first embodiment 10.

Regarding the catheter 110 specifically, however, it has particularly advantageous features. Because the leading half (10 French sub-section 167 and nose section 157) is only 75% of the diameter of the trailing half (13.5 French and transition sub-sections 165 and 166) inserting the catheter 110 into a patient's vein is made easier. The smaller diameter of the leading half of the bolus 120 also makes it more flexible, permitting the catheter 110 to travel around bends in the receiving vein more easily.

When it is in place in a patient, the catheter 110 also has other advantages. The venous ports 189, 193 and 201 are held away from the vein wall by the larger diameter 13.5 French sub-section 165. More blood is available around the venous ports 189, 193 and 201 than around the arterial port 137, making it less likely that blood will be pulled directly away from the venous ports by the arterial port 137 in the larger diameter 13.5 French sub-section 165.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A hemodialysis catheter, comprising:
   a) an elongated catheter tube including a tube body having a proximal end and a distal end;
   b) said tube body including a generally cylindrical wall enclosing a venous lumen and an arterial lumen separated by a septum;
   c) a longitudinally elongated bolus on said distal end of said tube body, said bolus including a bolus body having a tube connector section connected to said tube body, a passage section and a nose section, said nose section forming a bullet nose shaped, closed front end on said bolus body;
   d) said passage section containing a venous passage and an arterial passage, said venous passage communicating with said venous lumen and said arterial passage with said arterial lumen;
   e) a main venous port formed in one side of said bolus body adjacent said nose section and communicating directly with said venous passage;
   f) a second venous port formed in at least one of said bolus body and said tube body, said second venous port being circumferentially displaced about 180° from said main venous port around the axis of said catheter and communicating directly with at least one of said venous passage and said venous lumen;
   g) an arterial port formed in at least one of said tube body and said bolus body, said arterial port communicating directly with at least one of said arterial passage and said arterial lumen;
   h) both said tube body and said bolus body being formed of silicone; and i) directly opposite each of said ports is a stiffening arch formed by a bulge in said bolus body or said tube body bulge.

2. A hemodialysis catheter, comprising:
a) an elongated catheter tube including a tube body having a proximal end and a distal end;
b) said tube body including a generally cylindrical wall enclosing a venous lumen and an arterial lumen separated by a septum;
c) a longitudinally elongated bolus on said distal end of said tube body, said bolus including a bolus body having a tube connector section connected to said tube body, a passage section and a nose section, said nose section forming a closed front end on said bolus body;
d) said passage section containing a venous passage and an arterial passage, said venous passage communicating with said venous lumen and said arterial passage with said arterial lumen;
e) a main venous port formed in one side of said bolus body adjacent said nose section and communicating directly with said venous passage;
f) a second venous port formed in at least one of said bolus body and said tube body, said second venous port being circumferentially displaced about 180° from said main venous port around the axis of said catheter and communicating directly with at least one of said venous passage and said venous lumen;
g) an arterial port formed in at least one of said tube body and said bolus body, said arterial port communicating directly with at least one of said arterial passage and said arterial lumen;
h) said tube body and said bolus body each have a predetermined thickness where a corresponding port penetrates them;
i) said tube body and said bolus body opposite each of said ports is thicker than where it is not opposite a port;
j) each of said second venous port and said arterial port is longitudinally elongated so as to have a racetrack configuration; and
k) each of said second venous port and said arterial port has a semicircular side edge extending entirely around the port.

3. A catheter for insertion into a patient's vascular system, comprising:
a) an elongated catheter tube including a tube body having a proximal end and a distal end;
b) said tube body including a generally cylindrical wall enclosing a venous lumen and an arterial lumen separated by a septum;
c) a longitudinally elongated bolus on said distal end of said tube body, said bolus including a bolus body having a tube connector section connected to said tube body, a passage section and a nose section, said nose section forming a closed front end on said bolus body;
d) said passage section containing a venous passage and an arterial passage, said venous passage communicating with said venous lumen and said arterial passage with said arterial lumen;
e) a venous port formed in a side of said bolus body adjacent said nose section and communicating directly with said venous passage;
f) an arterial port formed in a side of one of said tube body and said bolus body, said arterial port communicating directly with at least one of said arterial passage and said arterial lumen; and g) directly opposite each of said ports is a stiffening arch formed by a bulge in said bolus body or said tube body.

4. The catheter of claim 3 further characterized in that:
a) said nose section includes a bullet nose which forms said closed front end.

5. The catheter of claim 3 further characterized in that:
a) said arterial port extends around said tube body to opposite edges which are substantially at the level of said septum.

6. The catheter of claim 4 further characterized in that:
a) said arterial port comprises a main arterial port formed in one side of said bolus body; and
b) said tube body has a second arterial port formed therein.

7. The catheter of claim 4 further characterized in that:
a) both said tube body and said bolus body are formed of silicone.

8. The hemodialysis catheter of claim 3 further characterized in that:
a) each of said second venous port and said arterial port is longitudinally elongated so as to have a racetrack configuration.

9. The hemodialysis catheter of claim 8 further characterized in that:
a) each of said venous port and said arterial port has a semi-circular side edge extending entirely around the port.

10. The hemodialysis catheter of claim 9 further characterized in that:
a) said tube body and said bolus body each have a predetermined thickness where a corresponding port penetrates them;
b) said tube body and said bolus body opposite each of said ports is thicker than where it is not opposite a port.

11. A catheter for insertion into a patient's vascular system, comprising:
a) an elongated tube including a body having a venous lumen and an arterial lumen extending therethrough from a proximal end to a distal end;
b) a longitudinally elongated tip on said distal end, said tip having a venous passage and an arterial passage therein;
c) a venous port formed in one side of said tip and communicating with said venous passage;
d) an arterial port formed in another side of said tip and communicating with said arterial passage;
e) said catheter tube and tip being formed of silicone; and
f) directly opposite each of said ports is a stiffening arch formed by a bulge in said tip.

12. The hemodialysis catheter of claim 11 characterized in that:
a) said tip includes a relatively larger diameter trailing portion and a relatively smaller diameter leading portion.

13. The hemodialysis catheter of claim 12 further characterized in that:
a) said main venous port is formed in said leading portion and said arterial port is formed in said trailing portion.

14. The hemodialysis catheter of claim 13 further characterized in that:
a) said arterial port is circumferentially displaced about 180° from said venous port around the axis of said catheter.

15. The hemodialysis catheter of claim 14 further characterized in that:
 a) said venous passage extends through both portions of said tip; and
 b) said arterial passage extends through said trailing portion but not said leading portion.

16. The hemodialysis catheter of claim 15 further characterized in that:
 a) said leading portion is 10 French size; and
 b) said trailing portion is 13.5 French size.

* * * * *